United States Patent
Lines

(10) Patent No.: US 10,391,096 B2
(45) Date of Patent: Aug. 27, 2019

(54) METHOD FOR TREATING THROMBOTIC DISORDERS USING QUERCETIN-CONTAINING COMPOSITIONS

(75) Inventor: Thomas Christian Lines, Wayland, MA (US)

(73) Assignee: Quercegen Pharmaceuticals LLC, Boston, MA (US)

( * ) Notice: Subject to any disclaimer, the term of this patent is extended or adjusted under 35 U.S.C. 154(b) by 0 days.

(21) Appl. No.: 13/272,508

(22) Filed: Oct. 13, 2011

(65) Prior Publication Data

US 2013/0095095 A1    Apr. 18, 2013

(51) Int. Cl.

| | |
|---|---|
| *A61K 31/352* | (2006.01) |
| *A61K 31/375* | (2006.01) |
| *A61K 31/445* | (2006.01) |
| *A61K 31/519* | (2006.01) |
| *A61K 31/7048* | (2006.01) |
| *A61K 45/06* | (2006.01) |
| *A61K 31/455* | (2006.01) |
| *A61K 31/4365* | (2006.01) |

(52) U.S. Cl.
CPC .......... *A61K 31/519* (2013.01); *A61K 31/352* (2013.01); *A61K 31/375* (2013.01); *A61K 31/4365* (2013.01); *A61K 31/455* (2013.01); *A61K 31/7048* (2013.01); *A61K 45/06* (2013.01)

(58) Field of Classification Search
CPC .. A61K 31/352; A61K 31/375; A61K 31/445; A61K 31/519; A61K 31/7048
See application file for complete search history.

(56) References Cited

U.S. PATENT DOCUMENTS

| | | | | |
|---|---|---|---|---|
| 6,121,249 | A * | 9/2000 | Weissman .............. | A61K 45/06 514/165 |
| 2006/0003947 | A1* | 1/2006 | Udell .............................. | 514/26 |
| 2006/0276393 | A1* | 12/2006 | Milburn et al. ................. | 514/12 |
| 2007/0248590 | A1* | 10/2007 | Milne et al. ................ | 424/130.1 |
| 2008/0032987 | A1* | 2/2008 | Lines ............................ | 514/249 |
| 2009/0163448 | A1* | 6/2009 | Powell ........................... | 514/154 |

FOREIGN PATENT DOCUMENTS

| | | |
|---|---|---|
| CN | 1507870 A | 6/2004 |
| CN | 1562096 A | 1/2005 |
| CN | 1706466 A | 12/2005 |
| CN | 1715277 A * | 1/2006 |
| CN | 101554379 A | 10/2009 |
| CN | 100581552 A * | 1/2010 |
| WO | WO-98/41195 A2 | 9/1998 |
| WO | WO-00/12085 A1 | 3/2000 |
| WO | WO-00/28986 A1 | 5/2000 |

OTHER PUBLICATIONS

Zhang et al., Linking inflammation and thrombosis: Role of C-reactive protein, World J Cardiol. Nov. 26, 2010; 2(11): 365-369.*
Ma et al., C-reactive protein (CRP) rise is associated with the development of acute events in a model of plaque rupture and thrombosis [Life Science Journal, 2008; 5(2): 21-24] (ISSN: 1097-8135).*
Gill et al., Human C-Reactive Protein Increases Cerebral Infarct Size After Middle Cerebral Artery Occlusion in Adult Rats,Journal of Cerebral Blood Flow & Metabolism 24:1214-1218, 2004.*
Ting-Chao Chou, Theoretical Basis, Experimental Design, and Computerized Simulation of Synergism and Antagonism in Drug Combination Studies; Pharmacol Rev 58:621-681, 2006.*
Cortellaro et al., The Plat Study: Hemostatic Function in Relation to Atherothrombotic Ischemic Events in Vascular Disease Patients Principal results, Arteriosclerosis and Thrombosis 1992;12:1063-1070.*
Feldman et al. Intravascular hemodynamic factors responisble for progression of coronary atherosclerosis and development of vulnerable plaque, Current Opinion in Cardiology 2000, 15:430-440.*
Zangari et al., Increased risk of deep-vein thrombosis in patients with multiple myeloma receiving thalidomide and chemotherapy, Blood, Sep. 1, 2001 z vol. 98, No. 5.*
Matsui et al., Snake venom proteases affecting hemostasis and thrombosis, Biochim Biophys Acta. Mar. 7, 2000;1477(1-2):146-56 (abstract).*
Conuz et al., Importance of Findings on the Initial Evaluation for Cancer in Patients with Symptomatic Idiopathic Deep Venous thrombosis, Ann Intern Med. 1996;125(10):785-793.*
Bucek et al., C-reactive protein in the diagnosis of deep vein thrombosis, British Journal of Haematology, 2002, 119, 385-389.*
Harwood et al., A critical review of the data related to the safety of quercetin and lack of evidence of in vivo toxicity, including lack of genotoxic carcinogenic properties, Food and Chemical Toxicology 45 (2007) 2179-2205.*
Fennerty, Venous thromboembolic disease and cancer, Postgrad Med J 2006;82:642-648.*
Edwards et al., "Quercetin Reduces Blood Pressure in Hypertensive Subjects," J. Nutr. 137:2405-2411 (2007).
Trout, David L., "Vitamin C and Cardiovascular Risk Factors[1-3]" Am J Clin Nutr 53:322S-5S (1991).
A. DiSanto et al., "Resveratrol and Quercetin Down-Regulate Tissue Factor Expression by Human Stimulated Vascular Cells," Journal of Thrombosis and Haemostasis, 1: 1089-1095 (2003).
Maclean et al "Dicumarol and Rutin in Retinal Vascular Disorders" American Journal of Ophthalmology vol. 30, pp. 1093-1108. 1947.

(Continued)

Primary Examiner — Michael G. Hartley
Assistant Examiner — Nabila G Ebrahim
(74) *Attorney, Agent, or Firm* — Cesari and McKenna, LLP

(57) ABSTRACT

A method for treating thrombotic disorders using a composition containing quercetin, together with one or more of vitamin $B_3$, vitamin C, and folic acid. Also disclosed is a method of improving the efficacy of a blood thinning medication by co-administering a composition containing quercetin, together with one or more of vitamin $B_3$, vitamin C, and folic acid to a subject being treated with a blood thinning medication.

10 Claims, No Drawings

(56) References Cited

OTHER PUBLICATIONS

Marshall "Ambulatory Therapy for Thrombophlebitis with Rutin and Vitamin C" American Journal of Surgery vol. 80, pp. 52-56. 1950.
Plamondon "Traitment Spectaculaire de la Thrombose de la Vein Centrale de la Retine par un Collyre a L'Echothiophate" Laval Medicale vol. 31, pp. 178-182. 1961.
Martin et al "Role of Protein Disulfide Isomerase in Thrombus Formation in a Collagen-Induced Pathway of Thrombus Formation" Blood vol. 116, p. 156. 2010.
Mahan et al "New Antithrombotics: The Impact on Global Health Care" Thrombosis Research vol. 127, pp. 518-524. 2011.
Kountchev et al "Reduction of D-Dimer Levels After Therapeutic Administration of Antithrombin in Acquired Antithrombin Deficiency of Severe Sepsis" Critical Care vol. 9, pp. 596-600, 2005.
Wells et al "Value of Assessment of Pretest Probability of Deep-Vein Thrombosis in Clinical Management" The Lancet vol. 350, pp. 1795-1798, 1997.

\* cited by examiner

METHOD FOR TREATING THROMBOTIC DISORDERS USING QUERCETIN-CONTAINING COMPOSITIONS

BACKGROUND

Thrombosis refers to the formation of a blood clot within the vascular system. Clot formation is a normal response to hemorrhage and helps to maintain hemostasis. If thrombosis occurs at the wrong place or at the wrong time, it can lead to reduced blood flow to critical organs such as the brain (stroke), lungs (pulmonary embolism), and myocardium (myocardial infarction). Venous thrombosis, which occurs mainly in the deep veins of the leg, often results in pulmonary embolism, when a portion of the clot flows through the circulation to the lungs. Atherothrombosis, or clots that form in arteries, lead to acute coronary syndrome, ischemic stroke, and limb ischemia.

Thrombus formation involves several sequential steps that typically begin following a skin laceration or a vascular injury. Circulating platelets first adhere to the site of injured endothelial cells and a series of events occurs that allows activation of these platelets. Activated platelets then recruit additional platelets to the site of injury, where they aggregate to form a plug until a stable clot forms. Inactive coagulation factors, which are always present and circulating in the bloodstream, are then sequentially activated in a process known as the coagulation cascade. The coagulation cascade ultimately leads to a stable fibrin-containing clot.

Thrombotic disorders are a group of inherited and acquired disorders that cause abnormal activation of the hemostatic system, leading to an increased risk of venous and arterial thrombosis. Cancer is among the acquired disorders that greatly increase the risk of thrombosis. Tumor cells, by expressing high levels of tissue factor on their surface, cause a hypercoagulable state. Tissue factor is required for initiating the just-mentioned coagulation cascade.

Among the factors involved in thrombus formation is protein disulfide isomerase (PDI). PDI is secreted by activated endothelial cells and platelets, after which it plays a critical role in thrombus formation. PDI can activate tissue factor, which leads to activation of the coagulation cascade, ultimately resulting in fibrin deposition and thrombus formation.

It is known that certain natural antioxidants, such as quercetin, inhibit both acute and chronic phases of free-radical induced diseases. Further, some natural antioxidants exhibit synergy in their reactions with biologically relevant oxygen species, e.g., hydroxyl radicals, superoxides, oxy-sulfurs, sulfur dioxide, and nitrogen dioxide.

Quercetin, in addition to its effects on free-radical induced diseases, is known to inhibit platelet aggregation in vitro. Quercetin administration is also known to reduce blood pressure in hypertensive patients.

SUMMARY

The present invention features a method for treating a thrombotic disorder by administering to a subject in need thereof an effective amount of a quercetin-containing composition, which also includes one or more of vitamin $B_3$, vitamin C, folic acid, and a blood thinning medication. In another aspect, the invention features a method for treating a thrombotic disorder using a composition containing quercetin, vitamin B3, vitamin C, and folic acid as the only active ingredients.

The invention also features a method for improving the efficacy of a blood thinning medication, in which an effective amount of the above-mentioned composition is administered to a subject taking a blood thinning medication. In still another aspect, the invention features a method for reducing the level of D-dimer in a subject by administering the above-mentioned composition.

The composition, either in dry form (e.g., powder or tablet) or in liquid form (e.g., beverage, syrup, or solution), can be a dietary supplement or a pharmaceutical formulation. The dietary supplement or the pharmaceutical formulation can be in the form of a tablet, a capsule, a soft chew, a gel, or a sterile injectable solution. The composition can also be a food product. Examples include tea (e.g., a tea drink and the contents of a tea bag), soft drinks, juice (e.g., a fruit extract and a juice drink), milk, coffee, jelly, ice cream, yogurt, cookies, cereals, chocolates, and snack bars.

The details of one or more embodiments of the invention are set forth in the description below. Other features, objects, and advantages of the invention will be apparent from the description and from the claims.

DETAILED DESCRIPTION

This invention is based, at least in part, on the unexpected findings that quercetin, together with one or more of vitamin $B_3$, vitamin C, and folic acid, exhibits synergistic inhibition of PDI activity and venous or arterial thrombus formation without leading to excessive bleeding following administration of a composition containing these ingredients to a subject.

Accordingly, the present invention features a method for treating a subject suffering from a venous or arterial thrombotic disorder by administering an effective amount of a composition containing quercetin and folic acid. In another embodiment, quercetin, vitamin $B_3$, and, optionally, folic acid may be used to treat a venous or arterial thrombotic disorder. In still another embodiment, quercetin, vitamin C, and, optionally, folic acid may be used to treat a venous or arterial thrombotic disorder. Further, a venous or arterial thrombotic disorder may be treated using a composition that includes quercetin, vitamin $B_3$, vitamin C, and, optionally, folic acid. In a preferred embodiment, a composition described above contains quercetin in the form of isoquercetin or rutin. In an additional preferred embodiment, a venous or arterial thrombotic disorder is treated by co-administering clopidogrel bisulfate and a composition containing quercetin, isoquercetin, or rutin, together with one or more of vitamin $B_3$, vitamin C, and folic acid.

The present invention also features a method for improving the efficacy of a blood thinning medication by administering an effective amount of the above-described compositions to a subject being treated with a blood thinning medication.

In one aspect, improving the efficacy of a blood thinning medication according to the present invention will allow for a subject to be treated with lower doses of blood thinners. For example, a subject being treated with a 75 mg per day dose of clopidogrel bisulfate, a blood thinning medication, can be treated with a lower dose (e.g., 50 mg, 25 mg, 10 mg, or less) if concurrently administered one of the above-described compositions. The ability to treat a subject using lower doses of blood thinning medication can, for example, advantageously reduce the time needed prior to surgery to withdraw blood thinning treatment, and can also reduce the time needed to restore antithrombotic activity post-surgery after treatment is resumed. Improving the efficacy of a blood thinning medication also refers to reducing the side effects associated with the blood thinning medication, e.g., reducing the amount of bleeding that occurs while a subject is being treated with the blood thinning medication.

Further, the invention includes a method for reducing the level of D-dimer in a subject with a higher than normal D-dimer level by administering the above-mentioned compositions. In addition, the composition can also be used to reduce the risk of a venous or arterial thrombotic event by prophylactic treatment of a subject at risk for a venous or arterial thrombotic event.

Without being bound by theory, the above described compositions may function to ameliorate thrombotic disorders by the following mechanisms.

Quercetin, together with one or more of vitamin $B_3$, vitamin C, and folic acid, synergistically inhibits the enzyme activity of protein disulfide isomerase (PDI). As mentioned above, PDI plays a critical role in the initiation of the coagulation cascade. By blocking this critical enzyme activity, quercetin can prevent thrombus formation. The antithrombotic activity of quercetin can be evaluated in humans by measuring D-dimer levels in plasma samples from patients treated with quercetin. D-dimer, a small protein fragment present in the blood, is a fibrin degradation product. The level of D-dimer in the blood increases after a thrombotic event due to its release from blood clots via fibrinolysis. Quercetin administration to hypertensive patients results in a reduction in the level of D-dimer in their blood, suggesting that quercetin reduces thrombus formation in these patients. Hypertensive patients are prone to thrombotic events.

Additionally, quercetin, together with one or more of vitamin $B_3$, vitamin C, and folic acid, synergistically lowers the blood pressure of a subject. High blood pressure is a major risk factor for cardiovascular complications, including stroke, myocardial infarction, and heart failure. High blood pressure can also lead to deep vein thrombosis as well as peripheral vascular disease, including both peripheral arterial disease and chronic venous insufficiency. Quercetin, together with one or more of vitamin $B_3$, vitamin C, and folic acid, can therefore reduce the risk of developing the just-mentioned conditions by lowering blood pressure.

The term "blood thinning medication" refers to an antiplatelet drug, e.g., clopidogrel bisulfate, heparin, warfarin, enoxaparin, abciximab, eptifibatide, tirofiban, prasugrel, ticlopidine, beraprost, prostacyclin, iloprost, treprostinil, aspirin, aloxiprin, carbasalate calcium, indobufen, triflusal, dipyridamole, picotamide, terutroban, cilostazol, cloricromen, ditazole; or an anticoagulant, e.g., acenocoumarol, coumatetralyl, dicoumarol, ethyl biscoumacetate, phenprocoumon, clorindione, diphenadione, phenindione, tioclomarol, bemiparin, certoparin, dalteparin, nadroparin, parnaparin, reviparin, tinzaparin, fondaparinux, idraparinux, danaparoid, sulodexide, dermatan sulfate, apixaban, betrixaban, edoxaban, otamixaban, rivaroxaban, bivalirudin, lepirudin, desirudin, argatroban, dabigatran, melagatran, ximelagatran, regimen 1 (REG1; a combination of RB-006, a Factor IXa antagonist, and its oligonucleotide active control agent RB-007), defibrotide, ramatroban, antithrombin III, or drotrecogin alfa.

The term "thrombotic disorder" refers to many distinct conditions that cause or increase the risk of a venous or arterial thrombotic event, including but not limited to, atrial fibrillation, thrombosis due to a mechanical heart valve, myocardial infarction, unstable angina, deep vein thrombosis, acute ischemic stroke, pulmonary embolism, atherosclerosis, factor V Leiden, antithrombin III deficiency, protein C deficiency, protein S deficiency, prothrombin gene mutation (G20210A), hyperhomocysteinemia, antiphospholipid antibody syndrome, anticardiolipin antibody, thrombosis syndrome, lupus anticoagulant syndrome, malignancy, major surgery, immobilization, oral contraceptive use, thalidomide use, especially in combination with dexamethasone, heparin-induced thrombocytopenia, pregnancy, myeloproliferative disorders, inflammatory bowel disease, nephrotic syndrome, paroxysmal nocturnal hemoglobinuria, hyperviscosity syndrome, Waldenstrom's macroglobulinemia, and trauma. The term "thrombotic disorder" also refers to thrombosis induced by cancer, e.g., multiple myeloma and other hematologic cancers, adenocarcinoma, cancer of the pancreas, stomach, ovaries, prostate, colon, lung, brain, breast, kidney, skin, cervix, and ear- nose- throat cancer.

The efficacy of quercetin is enhanced by vitamin $B_3$, vitamin C, or both. For example, a combination of quercetin, vitamin $B_3$, and vitamin C maintains quercetin levels in plasma up to five times those of quercetin alone or a combination of quercetin and vitamin $B_3$. Further, a combination of quercetin, vitamin $B_3$, and vitamin C results in a quercetin half life in plasma twice as long as that of quercetin alone and about one and a half times that of a combination of quercetin and vitamin $B_3$. See U.S. Pat. Nos. 7,745,486 and 7,745,487.

Typically, a subject who has or is at risk for developing a thrombotic disorder can be administered, once or periodically per day, with the composition in an amount that provides 20 mg to 3 g (preferably, 250 mg to 1 g) of quercetin. When vitamin $B_3$, vitamin C, or folic acid is included in a composition of this invention, it is preferred that each dose or serving contain 20 µg-3 g vitamin $B_3$, 200 µg-3 g vitamin C, or 40-3000 µg of folic acid.

The term "quercetin" refers to both quercetin aglycon and quercetin derivatives, e.g., quercetin-3-O-glucoside (isoquercetin), quercetin-5-O-glucoside, quercetin-7-O-glucoside, quercetin-9-O-glucoside, quercetin-3-O-rutinoside (rutin), quercetin-3-O-[α-rhamnosyl-(1→2)-α-rhamnosyl-(1→6)]-β-glucoside, quercetin-3-O-galactoside, quercetin-7-O-galactoside, quercetin-3-O-rhamnoside, and quercetin-7-O-galactoside. After digestion, quercetin derivatives are converted to quercetin aglycon and other active derivatives, which are absorbed in the body. The quantity of quercetin mentioned above refers to that of quercetin aglycon or the quercetin moiety of a quercetin derivative. Quercetin can be added to the composition either in a pure form or as an ingredient in a mixture (e.g., a plant extract). Examples of commercially available quercetin include QU995 (containing 99.5% quercetin) and QU985 (containing 98.5% quercetin) from Quercegen Pharma LLC (Newton, Mass.) and Merck KGaA (Brazil). "Vitamin $B_3$" mentioned herein includes vitamin $B_3$ in its various forms, including niacinamide, nicotinic acid, nicotinamide, inositol hexaniacinate. "Vitamin C" mentioned herein includes vitamin C (i.e., L-ascorbic acid, D-ascorbic acid, or both) and its salts (e.g., sodium ascorbate). "Folic acid" mentioned herein includes vitamin $B_9$, folate, pteroylglutamic acid, and L-methyl folate.

The composition administered in the methods of this invention can be in various forms. For example, it can be a soft chew composition that includes quercetin, niacinamide, ascorbic acid, sodium ascorbate, folic acid, sugar, corn syrup, sucralose, soy lecithin, corn starch, glycerin, palm oil, xylitol, carrageenan, FD&C Yellow #6, FD&C Yellow #5, and natural and/or artificial flavors. An exemplary serving of this soft chew composition (5.15 g) includes 250 mg of quercetin, 12.9 mg of vitamin $B_3$ (i.e., niacinamide), and 382.8 mg of vitamin C (i.e., L-ascorbic acid and sodium ascorbate). A subject can take one to eight servings (e.g., 4 servings) of this soft chew composition daily. The amounts taken can vary depending on, for example, the disorder or condition to be treated and the physical states of the subject. Another exemplary composition of this soft chew includes 5.25 wt % of quercetin, 0.25 wt % of vitamin $B_3$, and 7.81 wt % of vitamin C (i.e., L-ascorbic acid and sodium ascorbate) plus 200 μg of folic acid per chew.

When the above-described composition is in powder form, it can be used conveniently to prepare beverage, paste, jelly, capsules, or tablets. Lactose and corn starch are commonly used as diluents for capsules and as carriers for tablets. Lubricating agents, such as magnesium stearate, are typically included in tablets.

The oral bioavailability of quercetin in the above-mentioned capsule or tablet formulations can be improved by the use of certain additives. For example, a capsule or tablet can include acid treated gelatin, citrate, potassium hydroxide, and/or a cyclodextrin. A preferred amount of these additives per mg of quercetin is 0.01-0.5 mg potassium hydroxide, 0.01-0.7 mg acid treated gelatin, 0.1-1 mg citrate, and 0.01-1 mg of a cyclodextrin. Quercetin, in the presence of the additives, can have a solubility in an aqueous solution of 2-5%. Additionally, the pH of a quercetin-containing formulation with improved oral bioavailability can be between pH 7 and pH 12.

The composition administered in the methods of this invention can be a dietary supplement or a pharmaceutical formulation. As a dietary supplement, additional nutrients, such as minerals or amino acids may be included. A pharmaceutical formulation can be a sterile injectable or infusible solution that contains the composition together with pharmaceutically acceptable excipients. The composition can also be a food product. As used herein, the term "food" broadly refers to any kinds of liquid and solid/semi-solid materials that are used for nourishing humans and animals, for sustaining normal or accelerated growth, or for maintaining stamina or alertness. Examples of human food products include, but are not limited to, tea-based beverages, juice, coffee, milk, jelly, cookies, cereals, chocolates, snack bars, herbal extracts, dairy products (e.g., ice cream, and yogurt), soy bean product (e.g., tofu), and rice products.

The terms "improving," "treating," and "reducing" refer to the administration of an effective amount of a composition of the invention to a subject, who needs to improve one or more of the above-mentioned conditions or has one or more of the just-mentioned disorders, or a symptom or a predisposition of one of more of the disorders or conditions, with the purpose to improve one or more of these conditions, or to prevent, cure, alleviate, relieve, remedy, or ameliorate one or more of these disorders, or the symptoms or the predispositions of one or more of them. The term "administration" covers oral or parenteral delivery to a subject a composition of the invention in any suitable form, e.g., food product, beverage, tablet, capsule, suspension, and sterile injectable solution. The term "parenteral" refers to subcutaneous, intracutaneous, intravenous, intramuscular, intraarticular, intraarterial, intrasynovial, intrasternal, intrathecal, intralesional, and intracranial injection, as well as various infusion techniques. An "effective amount" refers to a dose of the composition that is sufficient to provide a therapeutic benefit (e.g., reducing the levels of PDI activity in the serum). Both in vivo and in vitro studies can be conducted to determine optimal administration routes and doses.

The compositions described above can be preliminarily screened for their efficacy in treating the above-described conditions by in vitro assays and then confirmed by animal experiments and clinic trials. Other suitable analytical and biological assays are apparent to those of ordinary skill in the art. For example, the effectiveness of the compositions described above can be measured by conducting in vivo or in vitro studies of PDI enzymatic activity.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating a thrombotic disorder, the method comprising administering to a subject in need thereof an effective amount of a composition that includes isoquercetin, vitamin B3, vitamin C, and folic acid, wherein the thrombotic disorder is venous thrombosis.

2. The method of claim 1, further comprising administering an anticoagulant.

3. The method of claim 1, wherein the venous thrombosis is deep vein thrombosis or pulmonary embolism; is associated with factor V Leiden, antithrombin III deficiency, protein C deficiency, protein S deficiency, prothrombin gene mutation (G20210A), thrombosis syndrome, major surgery, immobilization, oral contraceptive use, thalidomide use, pregnancy, myeloproliferative disorders, nephrotic syndrome, paroxysmal nocturnal hemoglobinuria, or trauma; or is induced by cancer.

4. The method of claim 2, wherein the anticoagulant is acenocoumarol, coumatetralyl, dicoumarol, ethyl biscoumacetate, phenprocoumon, clorindione, diphenadione, phenindione, tioclomarol, bemiparin, certoparin, dalteparin, nadroparin, parnaparin, reviparin, tinzaparin, fondaparinux, idraparinux, danaparoid, sulodexide, dermatan sulfate, apixaban, betrixaban, edoxaban, otamixaban, rivaroxaban, bivalirudin, lepirudin, desirudin, argatroban, dabigatran, melagatran, ximelagatran, regimen 1, defibrotide, ramatroban, antithrombin III, or drotrecogin alfa.

5. The method of claim 1, wherein the venous thrombosis is induced by cancer.

6. The method of claim 1, wherein the composition includes about 250 mg to about 1000 mg of isoquercetin.

7. The method of claim 1, wherein the composition includes about 20 μg to about 3 g of Vitamin B3.

8. The method of claim 1, wherein the composition includes about 200 μg to about 3 g of Vitamin C.

9. The method of claim 1, wherein the composition includes about 1000 μg to about 3000 μg of folic acid.

10. The method of claim 1, wherein the effective amount is sufficient to reduce the level of protein disulfide isomerase activity in the serum of the subject.

* * * * *